Figure 1:
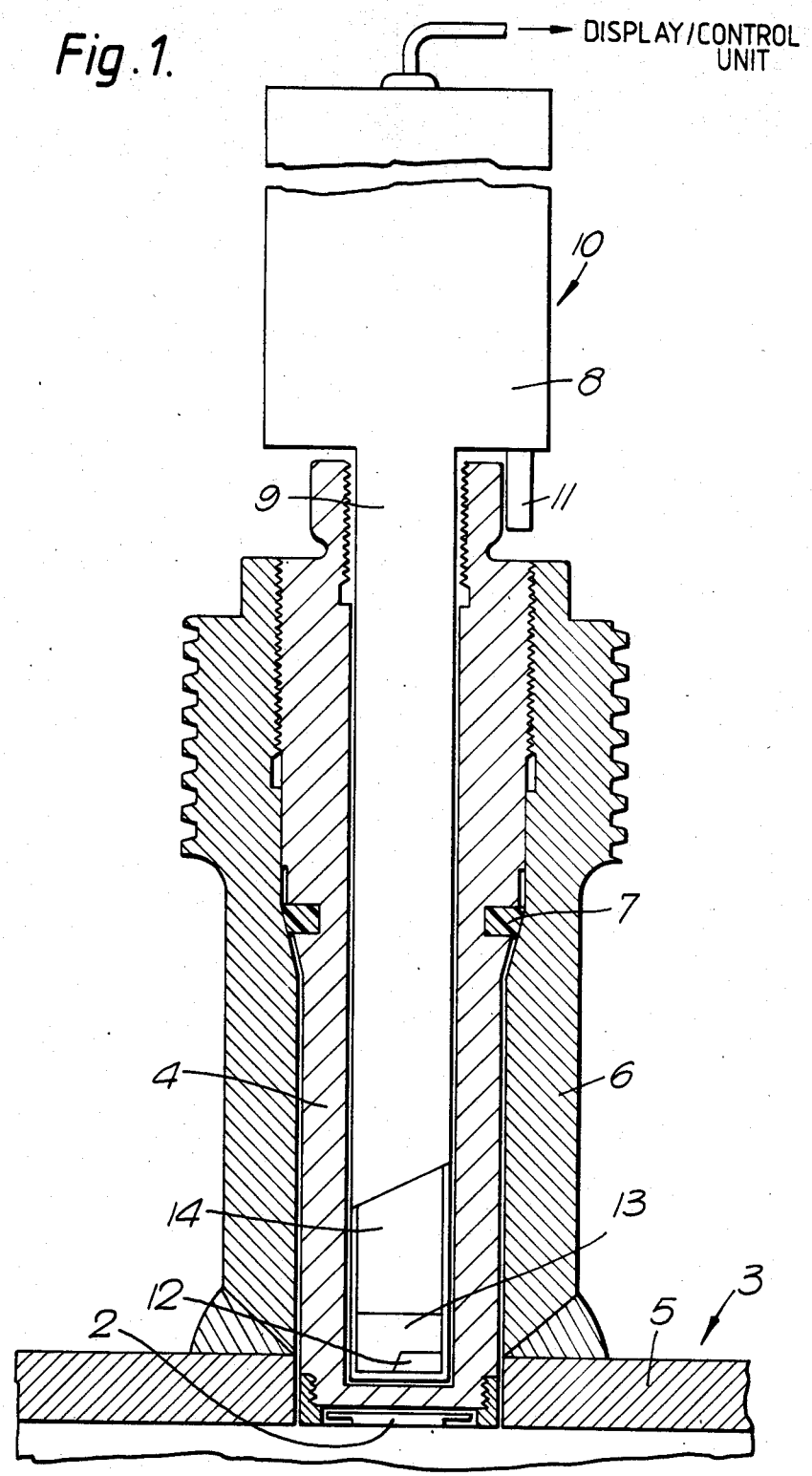

United States Patent [19]

Asher et al.

[11] Patent Number: 4,675,527
[45] Date of Patent: Jun. 23, 1987

[54] CORROSION MONITORING PROBE

[75] Inventors: James Asher, Marcham; Bruce C. Tofield; Malcolm R. Wormald, both of Abingdon; George B. Huxtable, Southmoor; Thomas W. Conlon, Abingdon, all of England

[73] Assignee: United Kingdom Atomic Energy Authority, London, England

[21] Appl. No.: 733,376

[22] Filed: May 13, 1985

[30] Foreign Application Priority Data

May 17, 1984 [GB] United Kingdom ................ 8412632

[51] Int. Cl.⁴ ............................................. G01N 17/00
[52] U.S. Cl. ................................. 250/393; 250/252.1; 250/363 R; 250/497.1; 250/498.1
[58] Field of Search ............... 250/358.1, 498.1, 497.1, 250/496.1, 252.1, 363 R, 361 R, 393; 378/160

[56] References Cited

U.S. PATENT DOCUMENTS 3,101,413  8/1963  Schaschl et al. .................... 250/393

FOREIGN PATENT DOCUMENTS 92484  7/1981  Japan ................................ 250/252.1
73761  4/1984  Japan ................................ 250/252.1

Primary Examiner—Janice A. Howell
Assistant Examiner—Constantine Hannaher
Attorney, Agent, or Firm—William R. Hinds

[57] ABSTRACT

A corrosion monitoring probe consisting of a housing for mounting a piece of radioactive material in a surface of a body the corrosion of which is to be measured so that the radioactive material is exposed to the same corrosive environment as the surface of the body, and means for measuring the intensity of ionizing radiation emitted by the radioactive material. The housing also contains a reference source of ionizing radiation and means for exposing a radiation detector which forms part of the means for measuring the intensity of ionizing radiation emitted by the radioactive material alternately to the radioactive material and the reference source of ionizing radiation.

5 Claims, 2 Drawing Figures

CORROSION MONITORING PROBE

The present invention relates to the monitoring of the loss of material from a solid article, and in particular to the monitoring by means of the technique known as thin layer activation analysis of the corrosion of a container or pipeline.

In this technique, a volume within a metal article the loss rate of which is to be determined, is rendered radioactive. Subsequently, either the decrease in the activity of the radioactive area of the metal article, or the activity arising from the loss of radioactive material from the radioactive area of the article to its environment is measured. In either case, the change in measured activity is a measure of the loss of radioactive material from the activated area of the article, and hence the rate of loss of material from the article as a whole, at least in the region of the activated area of the article.

A problem which can arise in the application of this technique is, how to gain access to a suitable area of the inside of a container or pipeline, particularly when it forms part of a plant. Other problems can arise from instrumental instability, which can arise from the widely varying environmental conditions under which the plant may operate.

According to the present invention there is provided a probe, for measuring the rate of loss of material from a solid body comprising means for mounting a coupon of radioactive material flush with a surface of a body the material loss rate of which is to be monitored, means for positioning a radiation detector so as to receive ionising radiation arising from the coupon, means for providing a reference source of ionising radiation of known intensity, and means for exposing the radiation detector alternately to ionising radiation arising from the coupon and that arising from the reference source of ionising radiation.

The means for exposing the radiation detector alternately to ionising radiation arising from the coupon and to that from the reference source of ionising radiation may comprise a holder for a small amount of radioactivity and means for moving the holder between a first position at which it is shielded from the radiation detector, and a second position at which ionising radiation can fall upon the radiation detector. Alternatively, the reference source can remain in a fixed position and a shutter can be used to shield and expose it.

Figure 2:
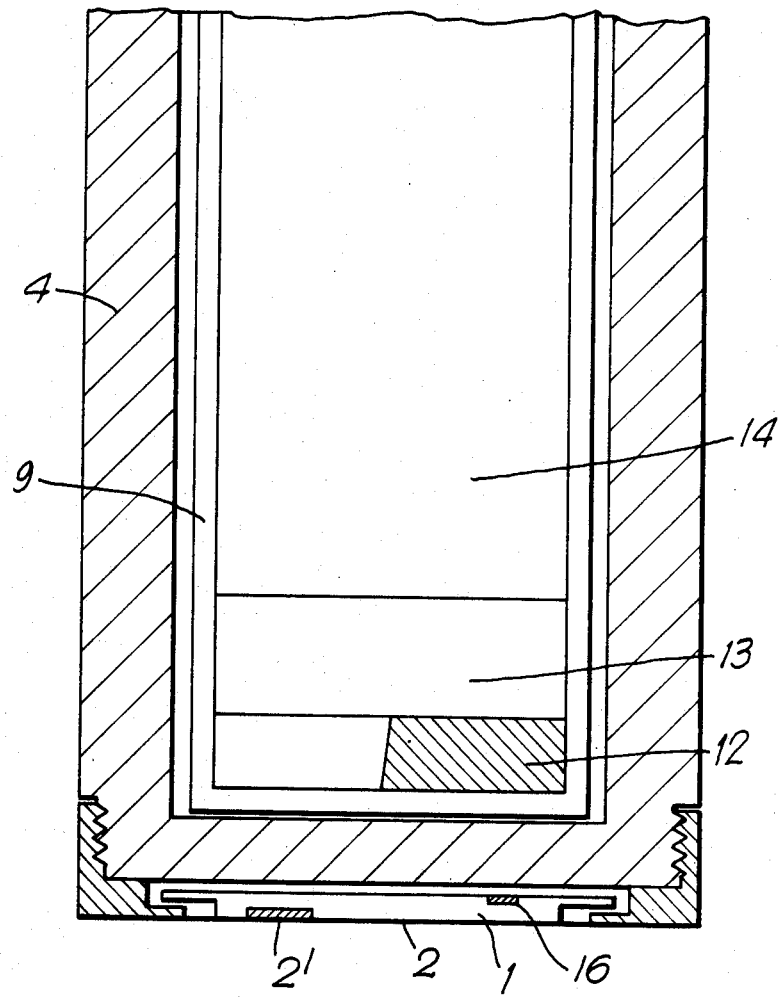

The invention will now be described, by way of example, with reference to the accompanying drawings in which, FIG. 1 shows a longitudinal section of an embodiment of the invention, and FIG. 2 shows an enlarged view of part of the embodiment of FIG. 1.

Referring to the drawings, a flush-mounted thin layer activation corrosion monitoring probe has a sensing element 1, known as a coupon, one surface 2 of which, at least is made radioactive to a well-defined depth over an area to provide a γ-ray source 2' by bombarding it with a beam of high energy radiation. The coupon 1 is made of the same material as a pipeline 3, the corrosion of which is to be measured. The coupon 1 is mounted at one end of a hollow plug assembly 4, which in turn is mounted in the wall 5 of the pipeline 3 by means of an access fitting 6 attached to the wall 5 of the pipeline 3. A pressure seal 7 is incorporated in the hollow plug 4 to avoid loss of fluid from the pipeline.

The dimensions of the hollow plug 4 and the access fitting 6 are so chosen that, when assembled, the exposed surface 2 of the coupon 1 is flush with the inner surface of the wall 5 of the pipeline 3. Inside the hollow plug 4 is a detector unit 8 which consists of a cylindrical housing 9 which extends from another housing 10 in which there is a photomultiplier and associated electronics (not shown). The housing 9 extends to the bottom of the hollow plug 4 and is rotatable therein. The position of the housing 9 is indicated and controlled by means of a peg 11 which projects from the housing 10 and locates the detector 13 in each of two measuring positions. At the end of the housing 9 remote from the housing 10 there is a semi-circular lead shutter 12, a scintillation-type γ-ray detector 13 and a light guide 14 arranged to convey light from the scintillation detector 13 to the photomultiplier. As can be seen from FIG. 2, in the unexposed surface of the coupon 1 there is inserted a source 16 of γ-rays of known intensity. It is advantageous that the two sources 2' and 16 utilise the same radio-isotope. The detector housing 9 is so located that in one position of the housing 9 the scintillation detector 13 is shielded from the γ-rays from the γ-ray source 16 by the lead shutter 12, and exposed to γ-rays from the source 2' and vice versa in the other position.

In use, the γ-ray intensity measured by the scintillation detector 13 is measured with each γ-ray source shielded, and then with it exposed, thus enabling spurious effects within the detector unit 8 to be eliminated and an absolute measurement of the loss of radioactive material from the surface 2 of the coupon 1 to be made.

The hollow plug assembly 4 may be made of a number of components fitted together instead of being a single body, so that it can be used with different access fittings 6. In this case it may be necessary to replace the locating peg 11 with a locating device which acts at the bottom of the hollow plug assembly instead of the top.

For use in inflammable environments where a high level of intrinsic safety is required, the light guide 14 may be replaced by a fibre optic bundle and the detector unit 8 removed to a region remote from the inflammable environment.

We claim:

1. A probe for measuring the rate of loss of material from a surface of a solid body, comprising a hollow plug assembly comprising a cylindrical outer sleeve adapted to be attached to the body the rate of loss of material from a surface of which is to be measured, a removable hollow inner member positioned within the outer sleeve and adapted to hold a coupon of radioactive material, the dimensional relationship between the outer sleeve and the inner member being such that on assembly the coupon is flush with the said surface of the body, means for positioning a radiation detector so as to receive ionising radiation arising from the coupon, means for providing a reference source of ionising radiation of known intensity and means for exposing the radiation detector alternately to ionising radiation arising from the coupon and that arising from the reference source of ionising radiation.

2. A probe according to claim 1 characterized in that the means for exposing the radiation detector alternately to ionising radiation arising from the coupon and to that from the reference source of ionising radiation comprises a holder for a small amount of radioactivity and means for moving the holder between a first position at which it is shielded from the radiation detector, and a second position at which ionising radiation can fall upon the radiation detector.

3. A probe according to claim 1 wherein the reference source is fixed in position and there is included a shutter and means for moving the shutter from a first position in which the radiation detector is shielded from radiation emitted by the reference source and a second position in which the radiation detector is exposed to the radiation emitted by the reference source.

4. A probe as claimed in claim 1 wherein the coupon in its assembled position is flush with and exposed to the same environment as said surface of the body, said reference source is located in the vicinity of but displaced from the radioactive material of the coupon so as not to be exposed to said environment, and said means for exposing the radiation detector alternately shields the detector from ionising radiation from the coupon radioactive material while exposing it to ionising radiation from the reference source in one position, and vice versa in another position.

5. A probe as claimed in claim 4 wherein the reference source is located on part of an unexposed surface of the coupon.

* * * * *